US008696321B2

(12) United States Patent
Zeqiri

(10) Patent No.: US 8,696,321 B2
(45) Date of Patent: Apr. 15, 2014

(54) CAVITATION DETECTION

(75) Inventor: Bajram Zeqiri, Middlesex (GB)

(73) Assignee: The Secretary of State for Trade and Industry, London (GB)

( * ) Notice: Subject to any disclaimer, the term of this patent is extended or adjusted under 35 U.S.C. 154(b) by 366 days.

(21) Appl. No.: 12/670,867

(22) PCT Filed: Jul. 25, 2008

(86) PCT No.: PCT/GB2008/002563
§ 371 (c)(1),
(2), (4) Date: Jun. 14, 2010

(87) PCT Pub. No.: WO2009/016355
PCT Pub. Date: Feb. 5, 2009

(65) Prior Publication Data
US 2010/0269574 A1 Oct. 28, 2010

(30) Foreign Application Priority Data
Jul. 27, 2007 (GB) .................................. 0714695.4

(51) Int. Cl.
*F04B 49/00* (2006.01)
(52) U.S. Cl.
USPC .............................. 417/44.1; 137/486; 702/54
(58) Field of Classification Search
USPC ................... 417/1, 44.1, 53; 702/54; 137/486
See application file for complete search history.

(56) References Cited

U.S. PATENT DOCUMENTS

| 3,548,640 | A |   | 12/1970 | Deason et al. |
| 3,792,204 | A | * | 2/1974  | Murayama et al. ........... 310/340 |
| 4,484,862 | A | * | 11/1984 | Jensen ............................. 417/36 |
| 5,074,150 | A | * | 12/1991 | Tirelli et al. .................... 73/590 |
| 6,330,525 | B1 | * | 12/2001 | Hays et al. ..................... 702/183 |
| 6,497,140 | B1 |   | 12/2002 | Zeqiri |
| 6,655,922 | B1 | * | 12/2003 | Flek ............................. 417/44.1 |
| 6,663,349 | B1 |   | 12/2003 | Discenzo et al. |

(Continued)

FOREIGN PATENT DOCUMENTS

| DE | 19848726      | 4/2000 |
| DE | 199 03 233 A1 | 8/2000 |

(Continued)

OTHER PUBLICATIONS

Zeqiri, et al.: "Studies of a Novel Sensor for Assessing the Spatial Distribution of Cavitation Activity within Ultrasonic Cleaning Vessels," Ultrasonics, Jan. 1, 2006, pp. 73-82, vol. 44, No. 1, IPC Science and Technology Press Ltd. Guilford, GB.

(Continued)

*Primary Examiner* — Eric Keasel
*Assistant Examiner* — Minh Le
(74) *Attorney, Agent, or Firm* — Thomas | Horstemeyer, LLP

(57) ABSTRACT

There is disclosed an apparatus and method for detecting cavitation in fluid machines, for example pumps (100). In one embodiment a piezoelectric gasket (102) is used as a sensor to sense cavitation. In some embodiments highpass filters (302), (501) are used to detect ultrasonic acoustic signals in about the MHz range. If the energy in the MHz range is excessive then cavitation is deemed to be occurring and the speed of a motor (110) may be reduced in proportion to the degree of cavitation deemed to be occurring. In another embodiment (FIG. 5) the energy in the MHz range is normalized against the energy in the kHz range. Other sensors (600, 701) are also disclosed.

16 Claims, 7 Drawing Sheets

(56) References Cited

U.S. PATENT DOCUMENTS

| | | | |
|---|---|---|---|
| 7,606,184 B2 * | 10/2009 | Liu et al. | 370/297 |
| 7,995,777 B2 * | 8/2011 | Yu et al. | 381/191 |
| 2003/0019297 A1 | 1/2003 | Fiebelkorn et al. | |
| 2003/0146675 A1 * | 8/2003 | Cuhat et al. | 310/319 |
| 2004/0000843 A1 * | 1/2004 | East | 310/331 |
| 2006/0207330 A1 * | 9/2006 | Adrian et al. | 73/632 |
| 2010/0141090 A1 * | 6/2010 | Yoon et al. | 310/320 |

FOREIGN PATENT DOCUMENTS

| | | |
|---|---|---|
| EP | 0 742 372 A1 | 11/1996 |
| FR | 2 404 850 A | 4/1979 |
| JP | 57105580 | 7/1982 |
| JP | 61 228344 A | 10/1986 |
| JP | 01 137979 A | 5/1989 |
| JP | 2003097410 | 4/2003 |

OTHER PUBLICATIONS

International Search Report for International Application No. PCT/GB2008/002563 filed on Jul. 25, 2008.

English translation of the Abstract for DE 19848726 published Apr. 27, 2000.

English translation of the Abstract for JP 57105580 published Jul. 1, 1982.

English translation of the Abstract for JP 2003097410 published Apr. 3, 2003.

* cited by examiner

__US 8,696,321 B2__

CAVITATION DETECTION

CROSS-REFERENCE TO RELATED APPLICATION

This application is a co-pending application which claims priority to PCT Application No. PCT/GB2008/002563, filed Jul. 25, 2008, herein incorporated by reference in its entirety. This application also claims priority to, and the benefit of, GB 0714695.4, filed Jul. 27, 2007, entitled "Cavitation Detection" herein incorporated by reference in its entirety.

The present invention is concerned with the detection of cavitation in fluid mechanisms. In particular, the present invention is concerned with the detection of cavitation in pumps for pumping a fluid (for example a supercritical fluid) or a liquid.

Cavitation is problematic phenomenon that can occur when a pump is operated such that the pressure inside the pump drops below the vapour pressure of a liquid being pumped. Bubbles of the vapourised liquid are formed. When the bubbles collapse, damage can be caused to the pump. During severe cavitation the noise of collapsing bubbles may be audible to a human. It would, however, be advantageous to detect the onset of severe and/or damaging cavitation so that the operating conditions of the pump can be modified (a minor amount of cavitation can be tolerated in some applications).

JP 11-037979 discloses a system for detecting cavitation in fluid mechanisms such as pumps. JP 11-037979 operates by comparing successive acoustic waveform cycles from a pump. Each waveform cycle is decomposed into a plurality of coefficients. The coefficients of successive acoustic waveform cycles are compared on a term-by-term basis by taking the dot product of successive acoustic waveforms. If successive acoustic waveform cycles are sufficiently similar then cavitation is deemed not to be occurring; if successive acoustic waveform cycles are sufficiently different then cavitation is deemed to be occurring.

According to an aspect of the present invention, there is provided:
  a transducer;
  a highpass filter for highpass filtering a signal from the transducer;
  a reference receiver for receiving a threshold;
  a comparator for comparing the highpass filtered signal with the threshold.

According to other aspects of the invention, there are provided acoustic sensors and a method of detecting cavitation.

An advantage of the present invention is that less signal processing is required compared to some prior art cavitation detection methods. Another advantage of some embodiments of the present invention is that they detect cavitation in the MHz range, which allows cavitation (or the onset of violent cavitation) to be more reliably identified.

In one embodiment of the present invention, the signal from the sensor is compared with a low pass filtered version of the signal from the sensor. An advantage of this embodiment is that it is less dependent on the level of the signal from the sensor and thus this embodiment is more tolerant of uncertainties in the acoustic coupling of the sensor to a pump being monitored.

DESCRIPTION OF PREFERRED EMBODIMENTS

Figure 1A:
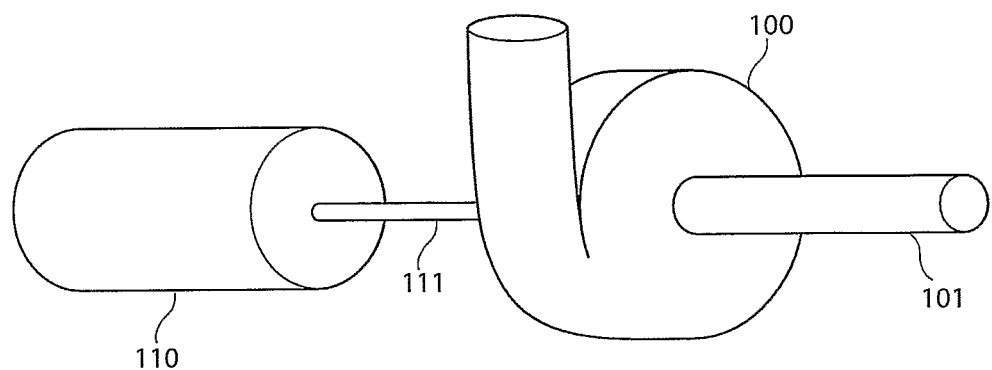
FIG. 1a shows a perspective view of a pump and a motor.
Figure 1B:
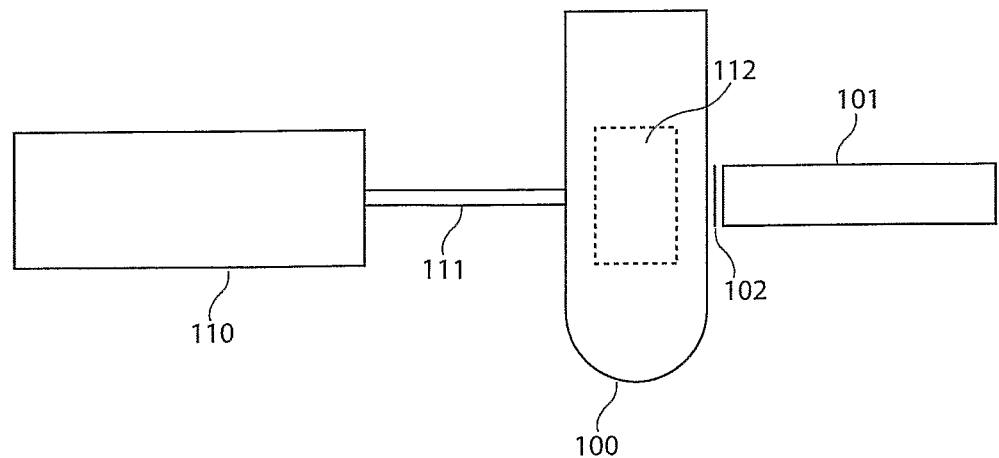
FIG. 1b shows a view of the pump and motor which enables a piezoelectric gasket to be seen.

FIGS. 1a and 1b show a pump 100 coupled to an inlet pipe 101 by a piezoelectric gasket 102. A motor 110 has a shaft 110 that drives an impellor 112 of the pump 100.

Figure 2:
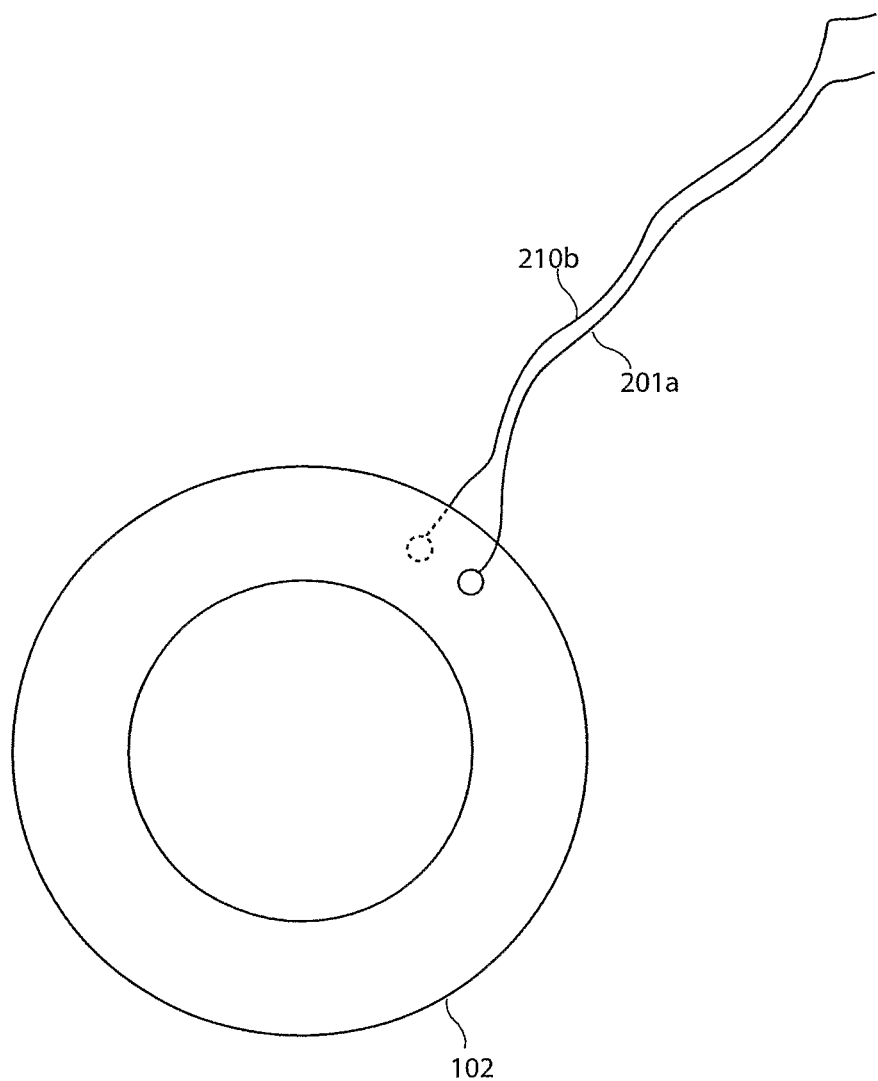
FIG. 2 shows a view of the piezoelectric gasket of FIG. 1b.

FIG. 2 shows a more detailed view of the piezoelectric gasket 102. In this embodiment the piezoelectric gasket 102 is annular and has two planar faces. One of the faces is used to form a fluid seal against the pump 100; the other face is used to form a fluid seal against the inlet pipe 101.

In this embodiment the piezoelectric gasket 102 comprises a polymer piezoelectric material, for example PVDF (polyvinylidene fluoride), having a thickness of 50 µm. Leads 201a, 201b are connected to respective faces of the gasket 102. The piezoelectric gasket 102 may be made from a single layer of film, a series of laminated layers or may posses a structured or patterned electrode. When the piezoelectric gasket 102 is clamped between the pump 100 and the inlet pipe 101, the piezoelectric gasket will convert acoustic signals from the pump into electrical signals. The piezoelectric gasket 102 can therefore be used to detect acoustic signals from the pump 100.

In other embodiments an electrostatic shield may be provided around the gasket 102 and/or the leads 201a, 201b to reduce the influence of external electrical signals.

In yet other embodiments, a ceramic piezoelectric material or a mixed polymer-ceramic composite material may be used instead of a polymer piezoelectric material. If a ceramic piezoelectric material is used then it may be necessary to coat the ceramic with a polymer such as rubber to prevent cracking of the ceramic when the ceramic piezoelectric material is clamped between the pump 100 and the inlet pipe 101.

An advantage of the use of a polymer piezoelectric material is that the thickness of the polymer may be more readily reduced than the thickness of a ceramic piezoelectric material. A relatively thin material will in general be better than a thicker material at detecting high frequency acoustic signals; this is because a thin material is small compared to the wavelength of a high frequency acoustic signal. For example, a 50 µm thick layer of PVDF has an upper frequency response of about 20 MHz and so cannot be effectively used to sense acoustic signals having a frequency of higher than about 20 MHz. At frequencies below 20 MHz the thickness of a thick 50 µm PVDF layer is significantly less than the wavelength of sound in, say, water. Also, a thinner material will have a higher resonant frequency (the first resonance occurs when the thickness of the material becomes equal to half of the acoustic wavelength), thus allowing higher frequency signals to be detected.

Figure 3:
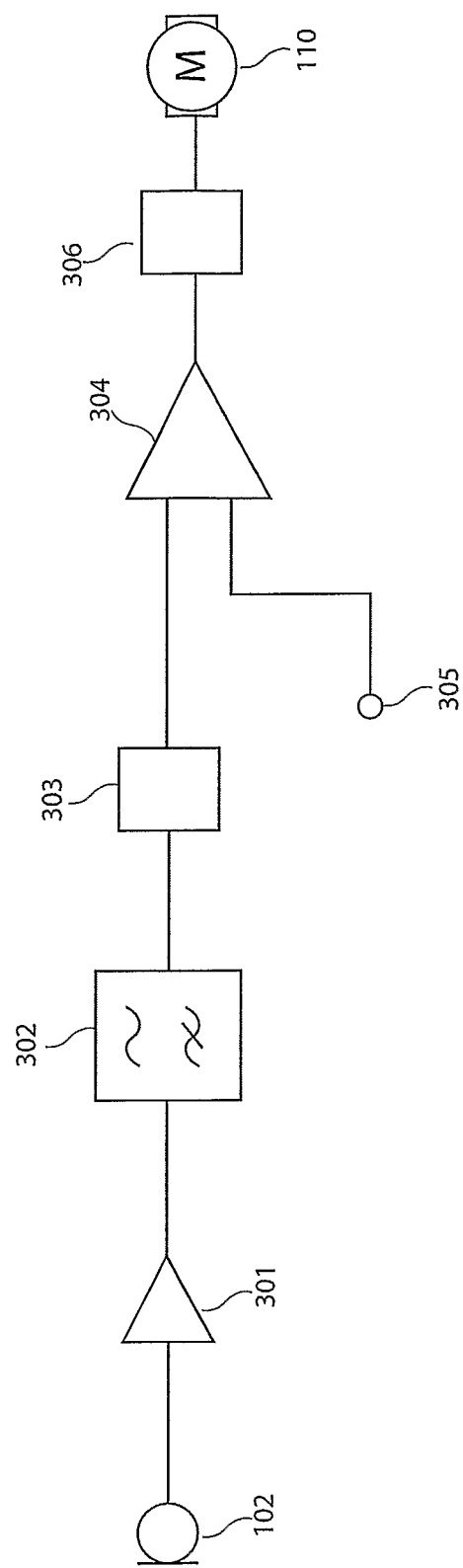
FIG. 3 shows a schematic illustration of a system which may be used to detect the onset of cavitation and reduce the speed of the motor if cavitation is detected.

FIG. 3 shows a schematic illustration of a system which may be used to detect the onset of cavitation and reduce the speed of the motor if cavitation is detected. FIG. 3 shows that the electrical signal from the piezoelectric gasket 102 is amplified by an amplifier 301 and is then filtered by a highpass filter 302. (In alternative embodiments, it may be preferable to filter and then amplify the signal from the piezoelectric gasket 102.) In this embodiment the highpass filter 302 attenuates signals having a frequency of less than 1 MHz. In this embodiment the highpass filter 302 is a second order (i.e. attenuation increases at 12 dB per octave) analogue filter although a digital filter could be used in alternative embodiments.

The output of the highpass filter 302 is connected to a detector 303. In this embodiment the detector 303 is an envelope detector and converts the signal from the highpass filter 302 into a voltage indicative of the strength of the signal from the highpass filter 302. In other embodiments, the detector 303 may comprise an amplitude sensor or an RMS (root-mean-square) detector.

The output of the detector 303 is connected to a comparator 304. The comparator 304 compares the voltage from the detector 303 with a reference signal received from a reference input 305. In this embodiment the comparator 304 subtracts the reference signal from the detected voltage. In other embodiments, the comparator 304 may divide the detected voltage by the reference signal to form a ratio.

In this embodiment, the output of the comparator 304 is connected to a motor controller 306 which controls the speed of the motor 110. In the event that the comparator 304 indicates excessive cavitation, the motor controller 305 reduces the speed of the motor 110 in order to reduce cavitation. In other embodiments, other methods may be used to reduce cavitation. For example, the head of pressure at the inlet to the pump 100 may be increased.

Figure 4:
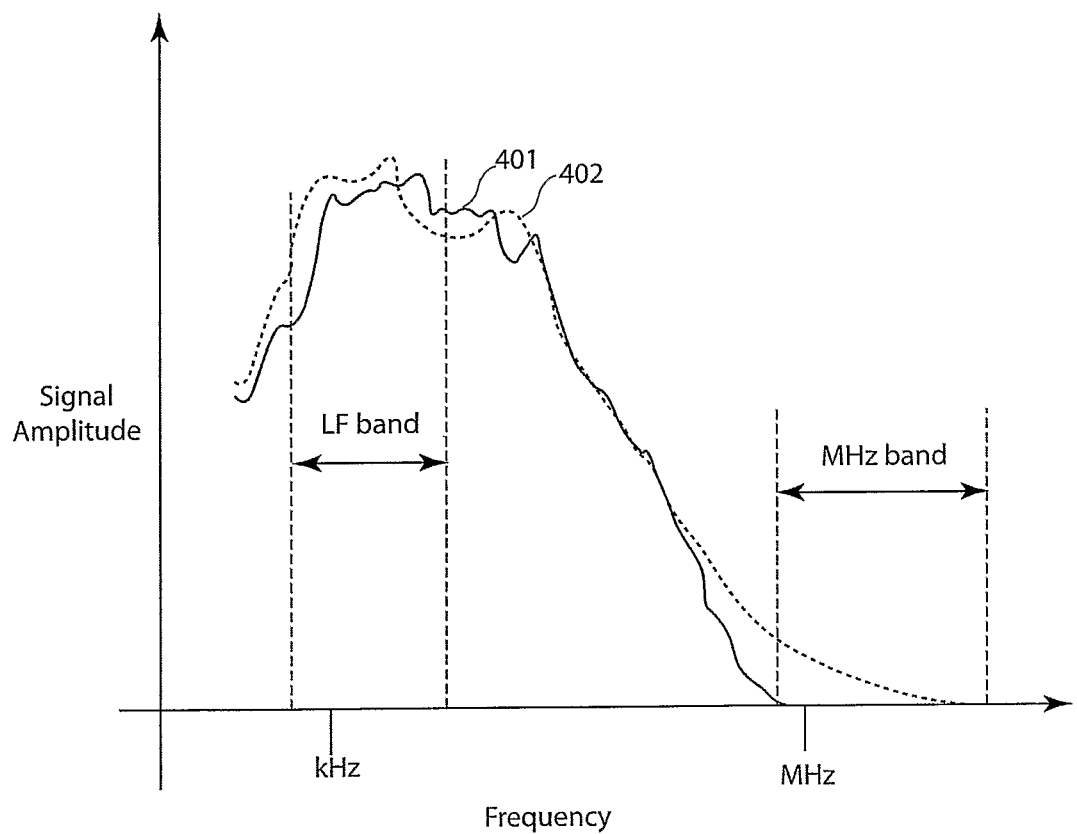
FIG. 4 shows an example of acoustic waveforms from a pump: (i) when the pump is operating without cavitation and (ii) during the onset of cavitation.

FIG. 4 shows an example of acoustic waveforms from the pump 100, and shows the amplitude of the acoustic waveform versus frequency. Curve 401 (the solid line) shows the amplitude of the acoustic waveform versus frequency when the pump is operating without significant cavitation. Curve 402 (the dotted line) shows the amplitude of the acoustic waveform versus frequency and during the onset of violent cavitation.

As can be seen from FIG. 4, during cavitation the amplitude of the acoustic waveform increases slightly at kHz frequencies but significantly at MHz frequencies. Prior art cavitation detectors generally attempt to detect cavitation having a frequency of 100 s of kHz. Embodiments of the present invention may detect cavitation having a frequency at least 0.5 MHz, at least 1 MHz, at least 2 MHz, at least 4 MHz or at least 8 MHz, by altering the cutoff frequency of highpass filter 302 as appropriate.

Figure 5:
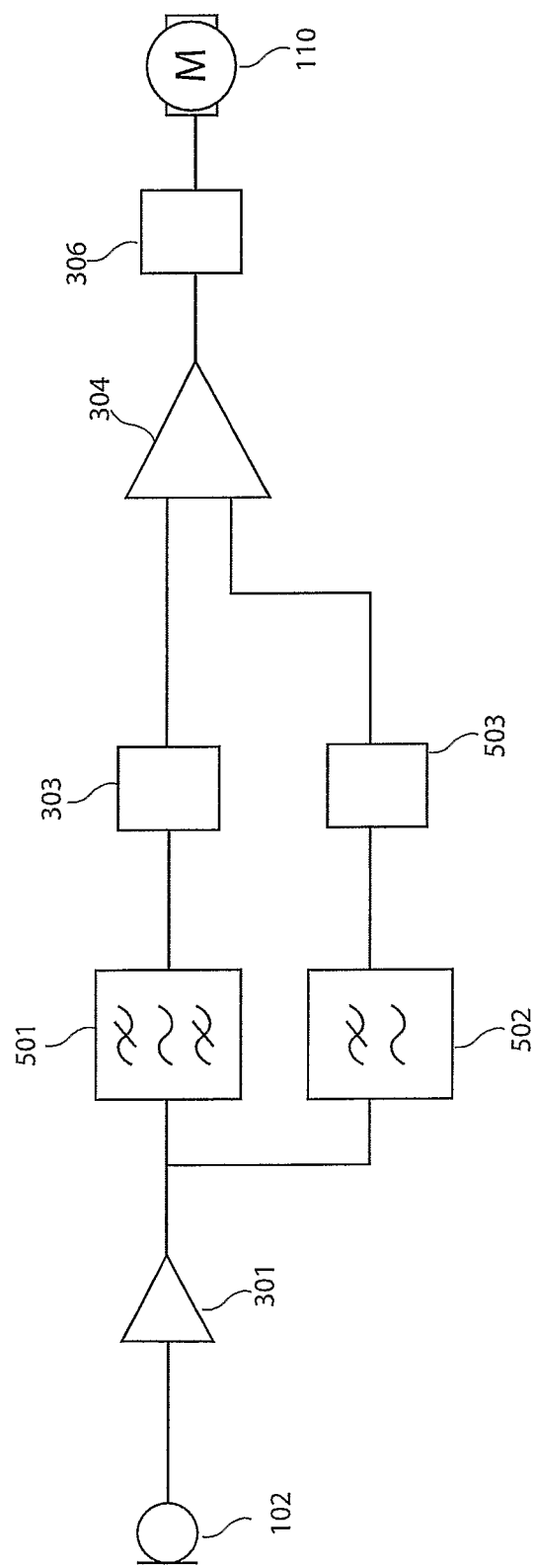
FIG. 5 shows a schematic illustration of a system based on FIG. 3 but which compares differently filtered versions of the signal from a sensor.

FIG. 5 shows a schematic illustration of a system based on FIG. 3 but which compares differently filtered versions of the signal from the piezoelectric gasket 102. FIG. 5 shows that the output from the amplifier 301 is filtered by a bandpass filter 501 (instead of the highpass filter 302). In this embodiment the bandpass filter 501 attenuates frequencies that lie outside the passband of 1 MHz to 5 MHz. The output from the amplifier 301 is also filtered by a lowpass filter 502, detected by a detector 503 and used as the reference input to the comparator 304. In this embodiment the lowpass filter 502 has a cutoff frequency of 1 kHz and thus attenuates frequencies higher than 1 kHz. In alternative embodiments, the cutoff frequency of the lowpass filter 502 may instead be at most 10 kHz, 100 kHz or 1 MHz.

As those skilled in the art will appreciate, the bandpass filter 501 can conceptually be regarded as a 1 MHz highpass filter in series with a 5 MHz lowpass filter (even though the bandpass filter 501 may actually be implemented as a single bandpass filter rather than as concatenated highpass and lowpass filters). Thus FIG. 5 includes a highpass filter function that is equivalent to the highpass filter 302 of FIG. 3. In some embodiments the upper frequency response of the piezoelectric gasket 102 may be used to define the lowpass filter of the bandpass filter 501.

The system of FIG. 5 compares the acoustic energy emanating from the pump 100 in the frequency range of 1 MHz to 5 MHz with the acoustic energy below 1 kHz. If there is an excess of energy in the range 1 MHz to 5 MHz then the pump 100 is deemed to be undergoing excessive cavitation and the motor controller 305 is used to reduce the speed of the motor 110 (and thus of the pump 100) accordingly.

An advantage of the system of FIG. 5 compared to the system of FIG. 3 is that FIG. 5 is more tolerant of imperfect acoustic coupling between the piezoelectric gasket 102 and the pump 100, and is also more tolerant of imperfect coupling due to the distance that the ultrasonic sound has to travel from the cavitating surface inside the pump 100 to the casing of the pump 100. The system of FIG. 3 cannot account for poor acoustic coupling (poor acoustic coupling could erroneously result in an indication that cavitation is not occurring). In contrast, the system of FIG. 5 normalises the energy in the frequency band 1 MHz to 5 MHz against the energy in the frequency range below 1 kHz. Thus if the piezoelectric gasket 102 is not well coupled to the pump 100, the signal in the frequency band 1 MHz to 5 MHz and the signal in the frequency range below 1 kHz will both be reduced. Thus the system of FIG. 5 can at least partially compensate for imperfect acoustic coupling.

Figure 6:
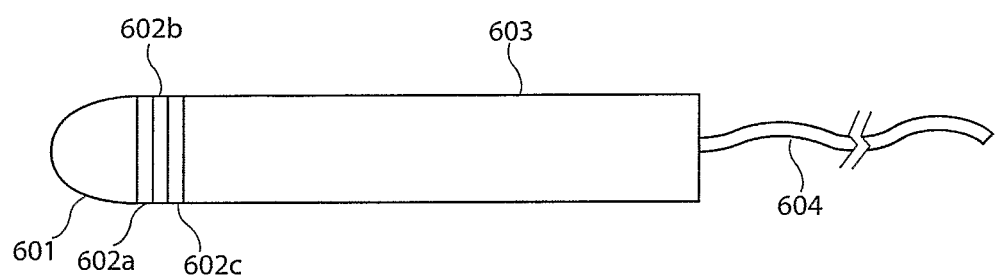
FIG. 6 shows a perspective view of a sensor that may be pressed against the housing of a pump in order to measure an acoustic signal from the pump.

FIG. 6 shows a perspective view of a sensor 600 that may be pressed against the housing of a pump in order to measure an acoustic signal from the pump. The sensor 600 may be used during the commissioning of a pump to determine operating conditions for the pump that do not involve excessive cavitation. Once the operating conditions have been determined, the sensor 600 may be more easily removed from the pump than, say, the piezoelectric gasket 102. On the other hand, an advantage of the piezoelectric gasket 102 is that it allows continuous real-time monitoring of the pump 100.

As shown, the sensor 600 comprises an acoustic coupler 601 which may be pressed against the housing of a pump. In this embodiment the acoustic coupler 601 is formed of rubber and couples acoustic energy to three PVDF layers 602a, 602b, 602c. In this embodiment each of the three PVDF layers 602 is substantially planar. The use of three PVDF layers improves the output voltage of the sensor 600 by a factor of about three but also reduces the upper frequency limit of the sensor 600 (compared to using a single PVDF layer; the reduction in the upper frequency limit is due to the increased thickness of the three PVDF layers compared to a single layer). In this embodiment the Shore hardness of the elastomeric coupler 601 is preferably in the range 10 to 20 although in other embodiments the Shore hardness may be less than 10 or more than 20.

The sensor 600 also has, in this embodiment, a metal shank 603 which acts as a grip portion to allow a user to hold the acoustic coupler 601 of the sensor 600 against the exterior of a pump or against pipes fastened to the pump. A lead 604 is used to connect the sensor 600 to circuitry (not shown), In alternative embodiments an acoustic sensor (not shown) may be fastened or bonded (for example using an adhesive)

against the exterior of a pump. In such embodiments the acoustic coupler 601 and/or the metal shank 603 may not be required.

Figure 7:
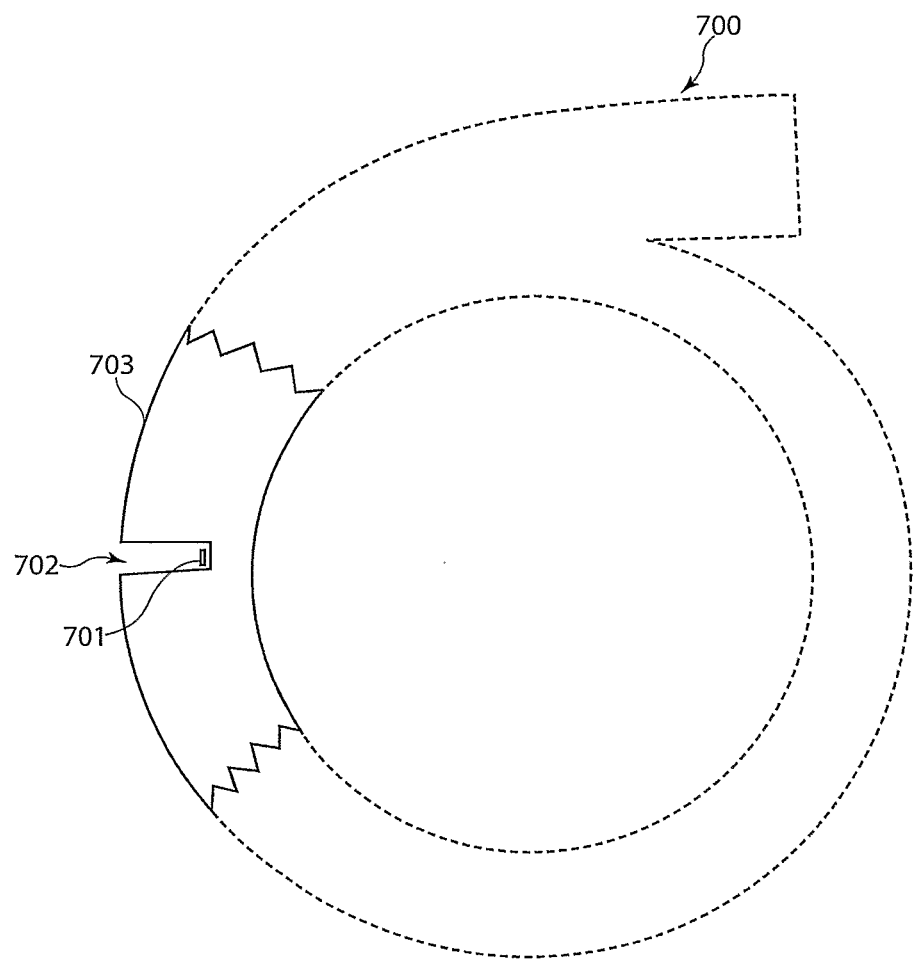
FIG. 7 shows a cross-sectional view of a portion of a pump in which an acoustic sensor has been embedded.

FIG. 7 shows a cross-sectional view of a portion of a pump 700 (the majority of the pump 700 is shown in phantom lines) in which an acoustic sensor 701 has been embedded. The acoustic sensor 701 is embedded in a recess 702 in the casing 703 of the pump 700. An advantage of this embodiment is that the acoustic sensor 701 is close to the fluid in which cavitation could occur. In contrast, the embodiment of FIG. 1 requires the acoustic signal to travel from the interior of the pump 100 to the piezoelectric gasket 102.

As those skilled in the art will appreciate, the present invention may be used to reduce cavitation in pumps, for example centrifugal pumps or axial pumps, or in other fluid mechanisms.

In some situations it may be advantageous to reduce the influence of electrical noise. The electrical signal from an acoustic sensor typically requires significant amplification and thus there is the risk of inadvertently picking up stray electrical signals. Although the electrostatic shield discussed above in connection with FIG. 2 may be sufficient, in other embodiments a calibration step may be performed. In such embodiments, the acoustic signal is measured under conditions under which it is known that no cavitation is occurring (for example when the motor 110 is stationary). If a signal, for example having a frequency of 2 MHz, is detected under the no-cavitation condition then an electrically configurable notch filter may be used to suppress the extraneous 2 MHz signal in order to avoid false alarms of cavitation when the motor 110 is running.

In some embodiments, for example when the acoustic sensor is to be fitted to plant machinery which is in use and cannot be stopped, it may be inconvenient to stop the motor(s) that drive pump(s). In such cases, it may be more convenient to detach the acoustic sensor from the body of a pump, thereby providing a "normalisation" signal in which cavitation is not occurring. Alternatively, the acoustic sensor may be allowed to dangle in air; the sensor may still pick up background electrical signals (particularly if the pump is in an electrically noisy environment) and the background electrical noise may thus be used as a normalisation signal.

In some embodiments, if the signal from the piezoelectric gasket 102 is sufficiently strong then it may not be necessary to use the amplifier 301.

There is disclosed an apparatus and method for detecting cavitation in fluid machines; for example pumps 100. In one embodiment a piezoelectric gasket 102 is used as a sensor to sense cavitation. In some embodiments highpass filters 302, 501 are used to detect ultrasonic acoustic signals in about the MHz range. If the energy in the MHz range is excessive then cavitation is deemed to be occurring and the speed of a motor 110 may be reduced in proportion to the degree of cavitation deemed to be occurring. In another embodiment (FIG. 5) the energy in the MHz range is normalised against the energy in the kHz range. Other sensors 600, 701 are also disclosed.

The disclosures in the abstract of the present application, and the entirety of GB 0714695.4 (from which the present application claims priority), are hereby incorporated by reference.

The invention claimed is:

1. A system for detecting an occurrence of cavitation during operation of a fluid mechanism, comprising:
   an acoustic sensor;
   a bandpass filter for filtering a signal from the acoustic sensor, the signal comprising a plurality of frequencies and the filter cutting off all of the frequencies that are less than 1 MHz and passing all of the frequencies up to 5 MHz;
   a first detector for providing a signal indicative of an energy in the bandpass filtered signal from the acoustic sensor;
   a lowpass filter for filtering the signal from the acoustic sensor;
   a second detector for providing a signal indicative of the energy in the lowpass filtered signal from the acoustic sensor;
   a reference receiver for receiving a reference value signal, wherein the reference receiver is arranged to receive the signal from the second detector as the reference value signal; and
   a comparator for comparing the signal from the first detector with the reference value signal and providing an indication if the signal from the first detector exceeds the reference value signal.

2. The system according to claim 1, comprising an amplifier to amplify the signal from the acoustic sensor.

3. The system according to claim 1, wherein bandpass filter comprises a highpass filter and a lowpass filter.

4. The system according to claim 3, wherein the lowpass filter of the bandpass filter comprises an upper response frequency of the acoustic sensor.

5. The system according to claim 1, wherein the lowpass filter has a cutoff frequency of at most one of 1 kHz, 10 kHz, 100 kHz or 1 MHz.

6. The system according to claim 1, wherein the acoustic sensor comprises a gasket comprising a piezoelectric material.

7. The system according to claim 6, wherein the piezoelectric material comprises a polymer piezoelectric material.

8. The system according to claim 7, wherein the gasket comprises PVDF.

9. The system according to claim 6, wherein the gasket is located at an inlet to a pump.

10. The system according to claim 1, wherein the acoustic sensor comprises an acoustic rubber coupler, one or more polymer piezoelectric layers and a grip portion.

11. The system according to claim 10, wherein the acoustic rubber coupler comprises rubber having a Shore hardness in a range of 10 to 20.

12. The system according to claim 1, wherein the acoustic sensor is provided in a recess in a casing of a pump.

13. The system according to claim 1 for detecting and controlling the occurrence of cavitation during operation of a fluid mechanism, further comprising a controller operable to control an operating condition of the fluid mechanism to reduce cavitation in the event that the comparator indicates that the signal from the first detector exceeds the reference value signal.

14. The system according to claim 13, wherein the controller comprises a motor controller and wherein the motor controller is operable to reduce a motor speed in the event that the signal from the first detector exceeds the reference value signal.

15. The system according to claim 14, comprising a motor.

16. The system according to claim 15, comprising a pump connected to the motor, wherein the acoustic sensor is located relative to the pump to sense cavitation occurring within the pump.

\* \* \* \* \*

UNITED STATES PATENT AND TRADEMARK OFFICE
CERTIFICATE OF CORRECTION

PATENT NO.        : 8,696,321 B2                               Page 1 of 1
APPLICATION NO. : 12/670867
DATED             : April 15, 2014
INVENTOR(S)       : Bajram Zeqiri It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 606 days.

Signed and Sealed this
Twenty-ninth Day of September, 2015

Michelle K. Lee
*Director of the United States Patent and Trademark Office*